(12) United States Patent
Hope

(10) Patent No.: US 10,238,109 B2
(45) Date of Patent: Mar. 26, 2019

(54) ANTI-PATHOGEN DEVICE

(71) Applicant: VIRUSTATIC LIMITED, Stockport (GB)

(72) Inventor: Paul Hope, Stockport (GB)

(73) Assignee: Virustatic Ltd., Manchester (GB)

( * ) Notice: Subject to any disclaimer, the term of this patent is extended or adjusted under 35 U.S.C. 154(b) by 0 days.

(21) Appl. No.: 14/904,464

(22) PCT Filed: Jul. 16, 2014

(86) PCT No.: PCT/GB2014/052169
§ 371 (c)(1),
(2) Date: Jan. 12, 2016

(87) PCT Pub. No.: WO2015/008062
PCT Pub. Date: Jan. 22, 2015

(65) Prior Publication Data
US 2016/0192652 A1    Jul. 7, 2016

(30) Foreign Application Priority Data

Jul. 16, 2013 (GB) .................................. 1312697.4

(51) Int. Cl.
| | | |
|---|---|---|
| *A01N 63/02* | (2006.01) | |
| *A01N 25/08* | (2006.01) | |
| *A01N 25/10* | (2006.01) | |
| *A01N 25/34* | (2006.01) | |
| *A01N 59/16* | (2006.01) | |
| *A01N 43/16* | (2006.01) | |
| *A01N 25/12* | (2006.01) | |
| *D06M 15/15* | (2006.01) | |
| *D06M 101/06* | (2006.01) | |
| *D06M 101/32* | (2006.01) | |
| *D06M 101/40* | (2006.01) | |

(52) U.S. Cl.
CPC ............ *A01N 43/16* (2013.01); *A01N 25/12* (2013.01); *A01N 63/02* (2013.01); *D06M 15/15* (2013.01); *D06M 2101/06* (2013.01); *D06M 2101/32* (2013.01); *D06M 2101/40* (2013.01)

(58) Field of Classification Search
None
See application file for complete search history.

(56) References Cited

U.S. PATENT DOCUMENTS

| | | |
|---|---|---|
| 5,851,395 A | 12/1998 | Kawase |
| 2005/0163825 A1 | 7/2005 | Naidu |
| 2007/0181499 A1 | 8/2007 | Roberts |
| 2010/0143490 A1 | 6/2010 | Roberts |

FOREIGN PATENT DOCUMENTS

| | | |
|---|---|---|
| JP | S56 123474 A | 9/1981 |
| JP | 2005 281231 A | 10/2005 |
| JP | 2012 111694 A | 6/2012 |
| WO | WO 2013/110940 A1 | 6/2013 |

OTHER PUBLICATIONS

Klemenčič et al.; Cellulose (2012) 19:1715-1729.*
Mikkelsen et al.; J. Agric. Food Chem; 2005, 53, 7673-7680.*
Google NPL search; downloaded Sep. 20, 2016.*
Castellino et al.; J. Biological Chem.; vol. 245, No. 1, Issue of Sep. 10, 1970; pp. 4269-4275. (Year: 1970).*
Tomšič et al.; J Sol-Gel Sci Technol.; (2008) 47:44-57. Published online Mar. 28, 2008.*
Lara et al.; Journal of Nanobiotechnology (2011); 9:30. Published Aug. 3, 2011.*
Demetriou et al.; Journal of Biological Chemistry; vol. 271, No. 22, pp. 12755-12761; published May 31, 1996.*
He et al.; Fish & Shellfish Immunology 31 (2011) 1247-1250. Published online Aug. 29, 2011.*
Baezinger et al.; J Biological Chemistry; vol. 254, No. 3, pp. 789-795; published Feb. 10, 1979.*
Kim et al.; Journal of the Faculty of Agriculture; pp. 133-143; published Mar. 1967.*
Wolfson et al.; Pediat. Res.; 5:514-517; published 1971.*
Mikkelson et al.; Journal of Agricultural and Food Chemistry; (2005); 53; pp. 7673-7680; Publised Sep. 10, 2005.*
Severi et al.; Microbiology (2007), 153, 2817-2822.*
Gamblin et al.; Journal of Biological Chemistry; vol. 285, No. 37, pp. 28403-28409; Sep. 10, 2010.*
Boce Zhang et al., "Development of silver/-lactalbumin nanocomposites: a new approach to reduce silver toxicity", Int'l J. Antimicrobial Agents, pp. 502-509, Jul. 21, 2011.
Neuberger M P et al., "Protein-mediated boundary lubrication in arthroplasty", Biomaterials, pp. 1165-1173, Apr. 1, 2005.
Tomsic B et al., "Antimicrobial activity of AgCl embedded in a silica matrix on cotton fabric", Carbohydrate Polymers, pp. 618-626, Feb. 24, 2009.
International Search Report dated Oct. 31, 2014 in related International Patent Application No. PCT/GB2014/052169.

* cited by examiner

*Primary Examiner* — Jeffrey T. Palenik
(74) *Attorney, Agent, or Firm* — Ryuh Patent Law; Steven Yu

(57) ABSTRACT

An anti-pathogen device may be useful as a wound dressing, an antibiotic sock, a mastitis cup, a tampon, or a window, door or bed cover. It comprises a carrier and a pathogen-binding component and a binding intermediate is attached to the carrier to facilitate binding of the pathogen-binding component to the carrier by forming a pathogen-binding construct with the pathogen-binding component. The pathogen binding construct may be lactoferrin, hololactoferrin, apolactoferrin, or asialolactoferrin. A carbohydrate binder binds the pathogen binding construct to the carrier.

16 Claims, 13 Drawing Sheets

Relationship between protein concentration (mg/mL) and absorbance at 280nm measured by microplate reader TECAN Infinite M200.

Comparison of the fetuin adsorption capability of cloth samples. The concentration of the fetuin in the solution before adsorption is marked as "Blank".

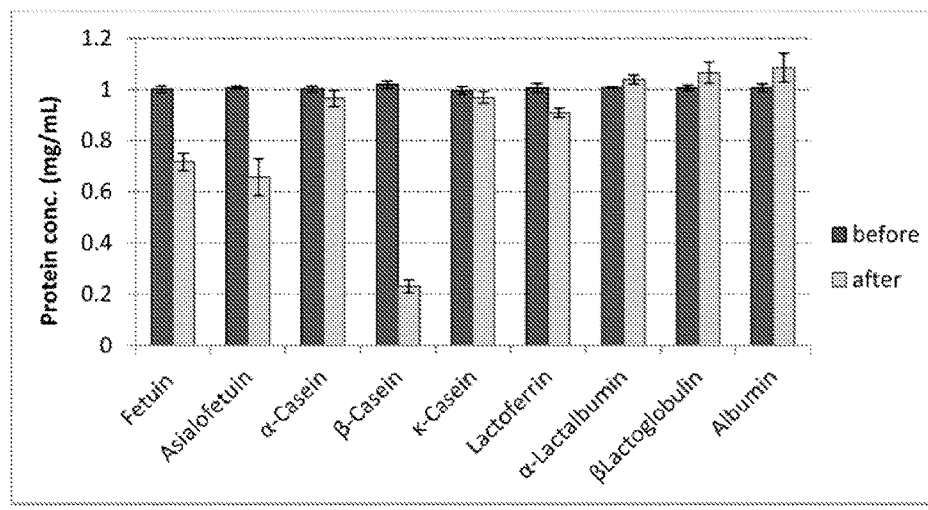

Proteins binding onto carbon cloth (Sample 16); purple columns indicates concentration of protein in the solution before dipping and yellow columns indicates concentration of protein in the solution after dipping period.

FIGURE 3

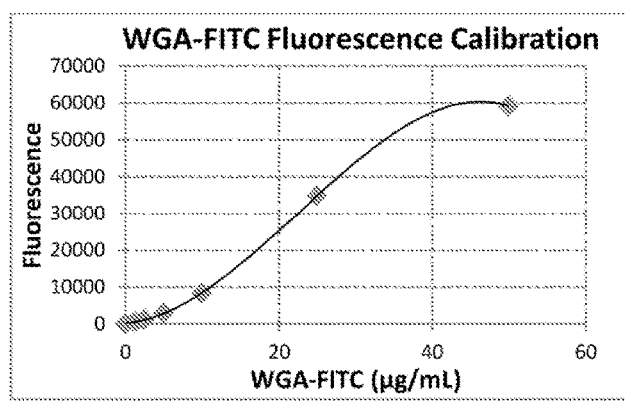

Calibration curve for fluorescence measurement of fluorescein tagged wheat germ agglutinin (WGA-FITC) in PBS solution (measured by TECAN Infinite M200 when excitation was at 488nm and emission at 530nm)

FIGURE 4

Calibration curve for fluorescence measurement of fluorescein tagged sambucus nigra lectin (SNA-FITC) in PBS solution (measured by TECAN Infinite M200 when excitation was set up at 488nm and emission at 530nm)

WGA-FITC binding onto carbon cloth (Sample 16) impregnated with fetuin, asialofetuin and bovine milk proteins by dipping method SNA-FITC binding onto carbon cloth (Sample 16) impregnated with fetuin, asialofetuin and bovine milk proteins by dipping method Comparison of the WGA-FITC binding onto the cloth samples impregnated with fetuin solution (1 mg/mL) and dried at 50-60°C

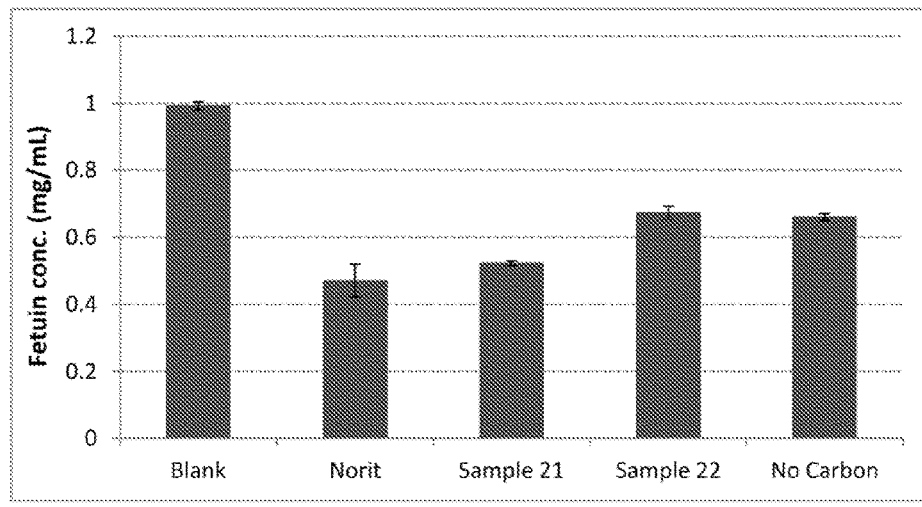

Comparison of the fetuin binding capability of Norit® with samples of carbon granules. The concentration of the fetuin in the solution before binding is marked as "Blank" and concentration of fetuin in the solution in an experiment without using activated carbon is marked as "No Carbon".

FIGURE 8a

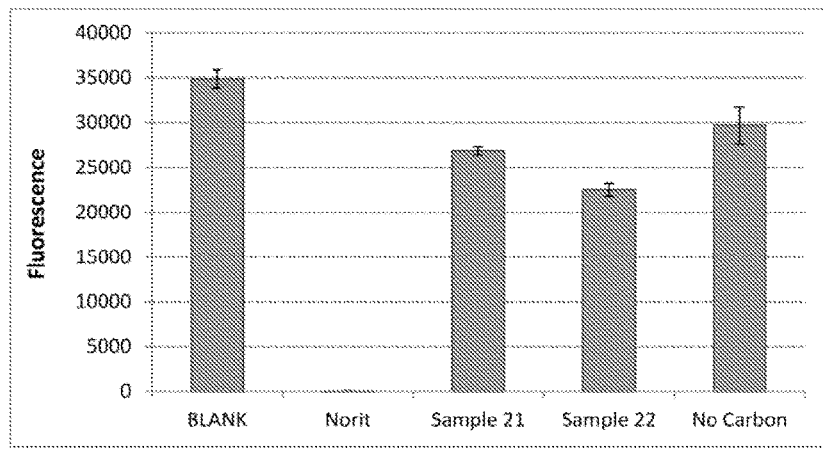

Comparison of the WGA-FITC binding onto the Norit® and samples of carbon granules impregnated with fetuin solution (1 mg/mL) and dried at 50-60°C. The fluorescence of the lectin solution before binding is marked as "Blank" and fluorescence of lectin solution in the experiment without using activated carbon is marked as "No Carbon". Columns showing lower fluorescence intensity values suggest stronger lectin binding.

FIGURE 8b

Schematic representation of flu virus capturing experiment

FIGURE 9

Plaque assay from flu virus binding experiments. Loaded $1.275 \times 10^7$ virus particles for 4 samples. Sample 1 – empty filter holder, sample 2 – neat Zorflex VB carbon cloth, sample 3 – fetuin-modified carbon cloth (0.6 mg fetuin/100 mg carbon cloth), sample 4 - fetuin-modified carbon cloth (2.5 mg fetuin/100 mg carbon cloth)

FIGURE 10

SNA-FITC binding onto carbon cloth (Sample 15) impregnated with fetuin solution (1 mg/mL), dried at 55°C and stored under different conditions; unspecific binding of SNA-FITC was blocked by dipping the cloth into BSA solution (5 mg/mL); from the equation y=1779.5x-1848 (the first picture) exact concentration of SNA-FITC in the solution before and after binding can be calculated

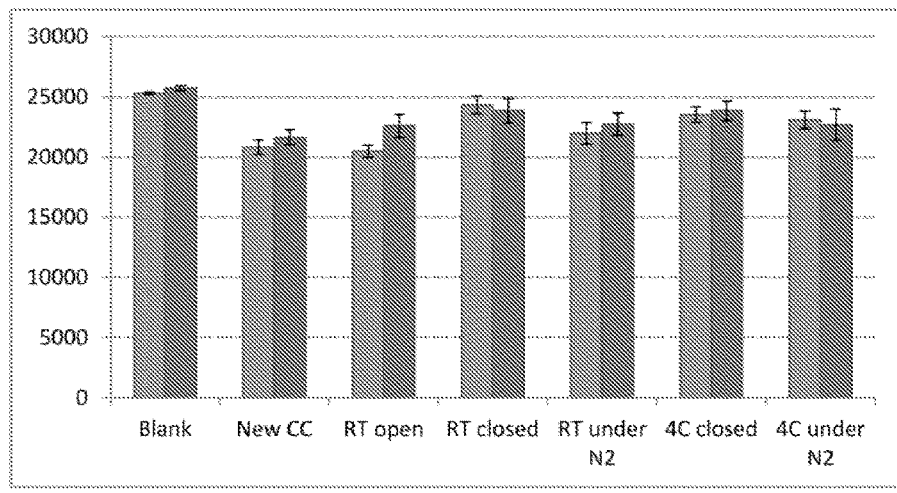

WGA-FITC binding onto carbon cloth (Sample 15) impregnated with fetuin solution (1 mg/mL), dried at 55°C and stored under different conditions; columns in darker colour indicates that unspecific binding of WGA-FITC was blocked by dipping the cloth into BSA solution (5 mg/mL) before the lectin assay

FIGURE 15

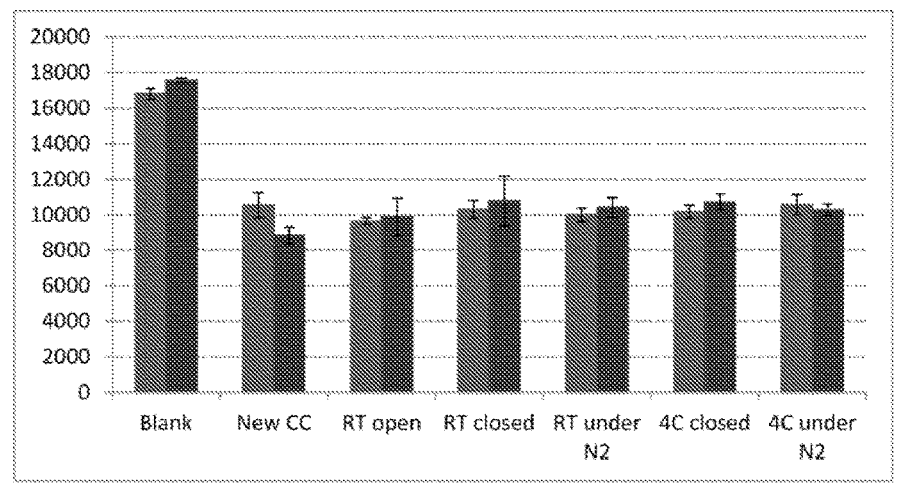

SNA-FITC binding onto carbon cloth (Sample 15) impregnated with fetuin solution (1 mg/mL), dried at 55°C and stored under different conditions; columns in darker colour indicates that unspecific binding of SNA-FITC was blocked by dipping the cloth into BSA solution (5 mg/mL) before the lectin assay

FIGURE 16

Apparatus for pressure drop test. Blower is a mechanical device moving air, control valve is used to control and adjust airflow (bleed on control valve is to minimise flow), carbon cloth is inserted in the middle of pipes with tapping, and Venturi at end of pipeline monitors flow rates.

Pressure Drop vs Flow Rate

Pressure Drop vs Flow Rate

ANTI-PATHOGEN DEVICE

BACKGROUND

The invention relates to the field of anti-pathogen device, methods of making anti-pathogen devices and uses of anti-pathogen devices, particularly for use with viruses and bacteria.

The use of sialic acid and its derivatives is generally known for capturing viruses. Sialic acid is a generic term used for a family of 9-carbon monosaccharides structurally deduced from neuraminic acid. Currently more than 50 different sialic acids have been found in nature with a variety of structures. They are widely found in higher animals and to a lesser extent in other species ranging from plants and fungi to yeasts and bacteria. In humans, sialic acids are mainly derived from Neu5Ac (N-Acetyl neuraminic acid) and usually occur as terminal units on cell-surface conjugates. Due to the occurrence as terminal molecules on cell-surfaces, sialic acids take part in a variety of complex and important physiological and pathological events including cellular and molecular recognition processes. Sialic acid also plays an important role in viral and bacterial infections.

Many viruses use sialic acid to enable them to recognise and bind to their target host cell membranes. The human influenza virus (Orthomyxoviridae), for example, has hemagglutinin (HA) protein on the virion protein coat or protruding through the envelope. The role of HA during viral entry into a host's cells is to bind to sialic acid receptors found on the cell membranes of human erythrocytes and the upper respiratory tract. Once the virus is bound to the cell membrane, a hole forms in the cell membrane and the virus particle and/or its genetic contents are released into the host cell, where viral reproduction begins. Similar mechanisms occur with viruses such as BK virus, adenovirus type 37, malaria, herpes simplex. HIV, cholera, sindbis, tumours, hepatitis, coxsackievirus A24 variant, rotavirus strains, and new and old world arenavirus (including ebola and rabies).

On the other hand, many other pathogens have evolved to decorate their own cell surfaces with sialic acid. Bacterium, in particular, incorporate sialic acid into their own cell surface features, although this characteristic is usually limited to those that live in association with higher animals (deuterostomes). The sialic acid-decorated cell surfaces of a bacterium enable them to disguise themselves and resist a host's innate immune response.

In order to defend against viral and bacterial infections, it is advantageous to be able to neutralise them or remove their infectious capability.

In view of the role that sialic acid plays in the infection pathway of both bacteria and viruses, it is considered helpful in the process of neutralisation or removal of their infectious capability. It is also thought that the combination of sialic acid with other components, such as a carrier with absorbance characteristics, or other anti-viral and/or anti-bacterial factors that could cause viral or bacterial death, might be advantageous.

However, sialic acid and its derivatives are not readily attached to other such carriers or factors. For example, there are a variety of other known components that are known for their anti-pathogen device and pathogen fighting abilities. One of these components is activated carbon and WO2011/062996 discloses an adaptable component having anti-pathogen device and virucidal properties, comprising a metal impregnated activated carbon cloth, an inner layer positioned along one side of the cloth and an outer layer positioned along the opposite side of the cloth. The layers can be attached together along all or a portion of a perimeter. The metal used is at least one of copper and silver, which are known as antimicrobials.

In addition, sialic acids are often 'weak' ligands for pathogens when they are 'free' (unbound). This has been observed between 'free' sialic acid and the HA protein.

It has therefore been an aim of the present invention to provide an improved anti-pathogen device using sialic acid.

SUMMARY OF THE INVENTION

In a first aspect of the invention there is provided an anti-pathogen device comprising a carrier and a pathogen-binding component, wherein a binding intermediate is attached to the carrier to facilitate binding of the pathogen-binding component to the carrier by forming a pathogen-binding construct with the pathogen-binding component.

With the present invention, the binding affinity of the pathogen-binding component for a pathogen is increased, in addition to the pathogen-binding component being advantageously attached to a carrier. This brings with it the possibility of delivering other advantageous factors to the pathogen via the carrier.

Preferably, the binding intermediate has a good binding affinity for the pathogen-binding component. Preferably, the binding intermediate also comprises a good binding affinity for the carrier.

Preferably, the pathogen-binding component is selected to have a binding affinity for a pathogen marker, e.g. a marker expressed by a pathogen.

Preferably, the pathogen-binding component comprises sialic acid or a derivative thereof.

Alternatively, the pathogen-binding component comprises a sialic-acid binding component, e.g. a component that recognises and binds to sialic acid or a derivative thereof.

During the course of the investigations, it has been discovered that when sialic acid is conjugated with an oligosaccharide, the HA is able to recognise and bind to the sialic acid more readily, e.g. it becomes a "strong" ligand for HA. In one aspect therefore, the binding intermediate comprises an oligosaccharide component.

During the course of the investigations, it has also been discovered that certain bacteria express sialic acid as a cell marker. When sialic acid is conjugated with an oligosaccharide, the HA is able to recognise and bind to the sialic acid more readily, e.g. it becomes a "strong" ligand for HA. In another aspect therefore, the pathogen-binding component comprises an oligosaccharide component.

During investigations, a high degree of specificity has been noted between HAs from different influenza viruses and it has been found that HAs often have a preference for sialic acid linked with an oligosaccharide at a particular position. For example, the HA of the human influenza virus preferentially binds alpha 2,6-sialic acid receptors and in contrast, HAs of the avian influenza virus appear to preferentially bind sialic acid linked with alpha 2,3-sialic acid receptors, whereas swine influenza viruses have the ability to bind both types of sialic acid receptors. This is also thought to be the case with other viruses such as BK virus, adenovirus type 37, malaria, herpes simplex. HIV, cholera, sindbis, tumours, hepatitis, coxsackievirus A24 variant, rotavirus strains, and new and old world arenavirus (including ebola and rabies).

Preferably, therefore, the oligosaccharide component is adapted to bind to sialic acid to provide 2,6-sialic acid receptors and/or 2,3-sialic acid receptors.

Preferably, the binding intermediate comprises a protein component. Preferably, the protein component is attached to the carrier. Preferably, the protein component is attached to the carrier by adsorption. Adsorption may be achieved by either immersing the carrier into a protein-component containing aqueous solution, by filtering a protein-component containing aqueous solution through the carrier, or by spraying the carrier with the protein-component.

The protein component may be denatured at the time of adsorption.

Preferably, the pathogen-binding construct comprises at least an oligosaccharide component and a protein component. Most preferably, the pathogen-binding construct also comprises a sialic acid or derivative thereof.

More preferably, the pathogen-binding construct comprises a glycoprotein. Most preferably, the glycoprotein further comprises sialic acid receptors thereon. The glycoprotein may comprise one of more of the following: fetuin; asialofetuin; albumin; Lactoferrin (LF); GMP (a sialic acid containing glycomacropeptide fragment of κ-casein 106Met-169Val); α-casein; β-casein; κ-casein; α-lactalbumin; or β-lactoglobulin.

Preferably the carrier comprises a textile or a cloth. Preferably the carrier textile or cloth comprises one or more of the following: cotton or carbon. Alternatively, the carrier comprises a veil or granules. Therefore, the carrier may comprise a carbon veil or carbon granules.

The cloth or textile carrier may be impregnated with a binder. Preferably, the cotton cloth is impregnated with a binder. The binder may be a carbohydrate polymer, which behaves as a reactive organic-inorganic binder. The binder may be based on a nanotechnological sol gel process. The binder may be iSys MTX (CHT, Germany). Alternatively the binder may be iSys LTX (CHT, Germany). More preferably, the cotton cloth is impregnated with an anti-microbial. The anti-microbial may be silver particles, which may be nanoparticles. The silver particles may be permanently embedded in the binder. The anti-microbial may be iSys Ag (CHT, Germany). The cotton cloth may comprise 100% cotton or a cotton mix. The cotton mix may comprise polyester. The cotton mix may comprise 50% cotton and 50% polyester.

The iSys MTX is thought to functionalise a cloth or textile surface and may be used in combination with other textile surfaces. When used in combination with iSys Ag, the surface finish is provided with an anti-microbial effect, since the Ag is permanently embedded in the MTX binder matrix. The same is the case for LTX.

Other carbohydrate polymers which function like iSys MTX (and indeed like iSys LTX) may also be used.

The carbon cloth may comprise activated carbon. Suitable forms of carbon include activated carbon, which is a form of charcoal (carbon) processed to have a very high porosity and so a very large surface area, and can include for example activated carbon cloth. Alternative forms of carbon include meso porous carbon and synthetic carbons such as nanotubes and fullerenes. Activated carbon is preferable for use in this invention, and more preferably activated carbon cloth is used. Activated carbon is widely used to adsorb organic or inorganic molecules from gases or liquids. It can be manufactured in many different forms like powered, granular or bead activated carbon. Activated carbon cloth is a special form of activated charcoal, originally developed by the British Ministry of Defence for use in chemical warfare suits. Nowadays, however, it can be used in numerous applications for example in many filtration devices or in medicine.

Preferably, the carbon (be it activated carbon (cloth) or otherwise) is impregnated with silver nanoparticles which help to deactivate viruses.

The carrier may comprise other mesoporous materials such as carbon silica and carbon cryogels.

The anti-pathogen device may be adapted for use with any pathogen which recognises and binds to sialic acid or a derivative thereof. Preferably, therefore, the anti-pathogen device is an anti-viral.

The anti-pathogen device may be adapted for use with any pathogen which expresses sialic acid or a derivative thereof. Preferably, therefore, the anti-pathogen device is an anti-bacterial.

According to a second aspect of the present invention there is provided an anti-viral device comprising:
  a carrier;
  a pathogen-binding component; and
  a binding intermediate.

wherein the pathogen-binding component comprises a sialic acid or a derivative thereof, and the binding intermediate is attached to the carrier to facilitate binding of the pathogen-binding component to the carrier by forming a pathogen-binding conjugate with the pathogen-binding component.

According to a third aspect of the present invention there is provided an anti-bacterial device comprising:
  a carrier;
  a pathogen-binding component; and
  a binding intermediate.

wherein the pathogen-binding component comprises an oligosaccharide with an affinity for conjugating with sialic acid or a derivative thereof, and the binding intermediate is attached to the carrier to facilitate binding of the pathogen-binding component to the carrier by forming a pathogen-binding construct with the pathogen-binding component.

It is to be appreciated that the features discussed in relation to the first aspect of the invention also apply to the second and third aspects of the invention.

According to a fourth aspect of the present invention there is provided a method of making an anti-pathogen device, comprising the steps of:
  a) providing a carrier;
  b) providing a pathogen-binding component;
  c) providing a binding intermediate;
  d) attaching the pathogen-binding component to the binding intermediate to form a pathogen-binding construct; and
  e) attaching the construct to the carrier.

Preferably, the pathogen-binding component comprises either an oligosaccharide with binding affinity for sialic acid or derivative thereof, or sialic acid or derivative thereof.

Preferably, where the pathogen-binding component comprises an oligosaccharide with binding affinity for sialic acid or derivative thereof, the binding intermediate comprises a protein component.

Preferably, where the pathogen-binding component comprises a sialic acid or derivative thereof, the binding intermediate comprises an oligosaccharide component and a protein component.

Preferably, where the device is intended for binding to a virus, the pathogen-binding construct comprises a sialylated glycoprotein.

Preferably, where the device is intended for binding to bacteria, the pathogen-binding construct comprises a desialylated glycoprotein.

Preferably in step (e), the pathogen-binding construct is adsorbed onto the carrier.

In step (e), the carrier may be exposed to a pathogen-binding construct comprising a conjugated monosaccharide having a sialic acid or derivative thereof thereon. This may be achieved by dipping the carbon into aqueous solution of pathogen-binding construct. The dipping period may comprise at least 20 minutes. Alternatively, an aqueous solution of pathogen-binding construct may be filtered through the carrier. Alternatively still, an aqueous solution of pathogen-binding construct may be sprayed onto the carrier.

The protein component may be denatured in any suitable fashion, prior to step (e). This may in some cases improve adsorption. Denaturing the protein component may comprise exposure to a detergent (e.g. a cationic detergent, preferably hexadecyltrimethyl ammonium bromide or sodium dodecyl sulphate), by using a phosphate buffered saline (PBS), or exposure to heat.

The carrier may be dried prior to step (e). This may also improve adsorption.

Preferably, the protein-binding construct is adsorbed onto the carrier in an amount of about 0.1-1 mg of sialic acid per gram of end product.

According to a fifth aspect of the present invention there is provided a method of making an anti-viral device comprising the steps of:
a) providing a carrier;
b) providing a pathogen-binding component comprising a sialic acid or a derivative thereof;
c) providing a binding intermediate;
d) attaching the pathogen-binding component to the binding intermediate to form a pathogen-binding conjugate; and
e) attaching the conjugate to the carrier.

According to a sixth aspect of the present invention there is provided a method of making an anti-bacterial device comprising the steps of:
a) providing a carrier;
b) providing a pathogen-binding component comprising an oligosaccharide with an affinity for conjugating with sialic acid or a derivative thereof;
c) providing a binding intermediate;
d) attaching the pathogen-binding component to the binding intermediate to form a pathogen-binding construct; and
e) attaching the construct to the carrier.

It is to be appreciated that the features discussed in relation to the fourth aspect of the invention also apply to the fifth and sixth aspects of the invention.

According to a seventh aspect of the invention there is provided use of an anti-pathogen device according to the first aspect of the invention, anti-viral device according to the second aspect of the invention or and anti-bacterial device according to the third aspect of the invention as a pathogen-capture mechanism.

The pathogen capture mechanism may comprise a filter. The filter may be used in a facemask, in an air conditioning unit, in blood filtration, in furnishings, surface coverings or body coverings.

The invention also provides a wound dressing; a sock; a mastitis cup; a tampon; a window, door or bed cover for use in hospitals or agricultural buildings comprising the device as set out in the first to third aspects of the invention.

Preferably the wound dressing, antibiotic sock, mastitis cup, tampon, window, door or bed cover comprises as a pathogen binding component lactoferrin, hololactoferrin, apolactoferrin, or asialolactoferrin and further comprises a carbohydrate binder for binding the pathogen binding component to the carrier.

BRIEF DESCRIPTION OF THE FIGURES

The invention will now be illustrated by reference to the following figures and examples:

FIG. 3 is a graphical representation of the concentrations of various glycoproteins remaining in solution when being adsorbed onto a cloth carrier;

FIG. 4 is a graphical representation of the relationship between WGA-FITC (tag) concentration and fluorescence (calibration);

FIG. 8a is a graphical representation of the fetuin concentration of remaining solutions following exposure to carrier carbon granules made according to the present invention;

FIG. 8b is a graphical representation of the concentrations of WGA-FITC (tag) remaining in solution following exposure to carrier carbon granules made according to the present invention;

FIG. 9 is a schematic representation of an apparatus for an influenza virus capturing experiment using devices of the present invention as air filters;

FIG. 10 is a graphical representation of a plaque assay following the influenza virus experiment;

FIG. 15 is a graphical representation demonstrating the WGA-FITC binding ability of a carbon cloth-fetuin device made according to the invention kept under various conditions 5 months following creation (longevity testing) following treatment with BSA;

FIG. 16 is a graphical representation demonstrating the SNA-FITC binding ability of a carbon cloth-fetuin device made according to the invention kept under various conditions 5 months following creation (longevity testing) following treatment with BSA;

SPECIFIC DESCRIPTION OF THE INVENTION

Figure 1:
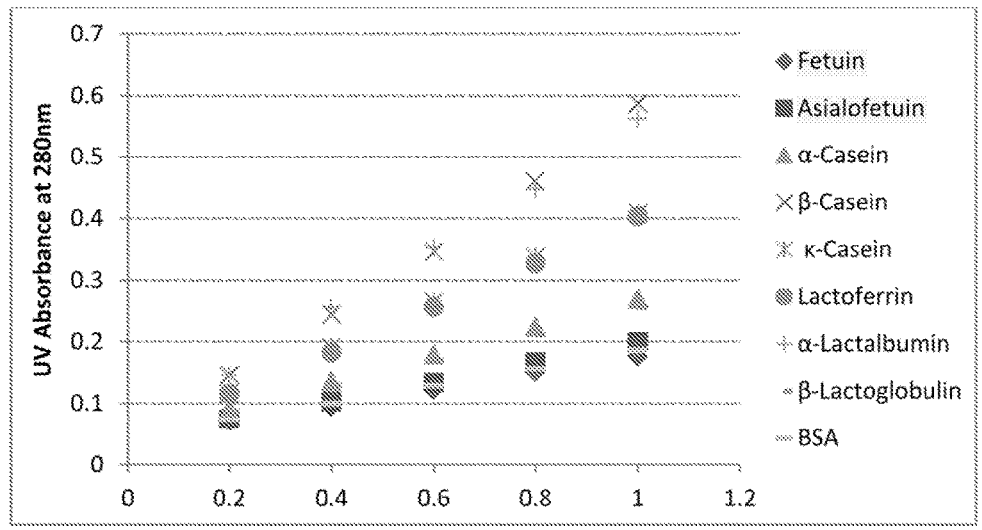
FIG. 1 is a graphical representation of the relationship between glycoprotein concentration and adsorbance of UV (calibration)

The present invention comprises an anti-pathogen device comprising a carrier and a pathogen-binding component, wherein the device comprises a binding intermediate attached to the carrier to facilitate binding of the pathogen-binding component to the carrier by forming a pathogen-binding construct with the pathogen-binding component.

In one embodiment, the invention may comprise an anti-viral device, in which case the pathogen-binding component comprises a sialic acid or a derivative thereof, and the binding intermediate forms a pathogen-binding conjugate with the pathogen-binding component.

In another embodiment, the invention may comprise an anti-bacterial device, in which case the pathogen-binding component comprises an oligosaccharide with an affinity for sialic acid or a derivative thereof, and the binding intermediate forms a pathogen-binding construct with the pathogen-binding component.

Carriers

For the purpose of the invention, a variety of different carrier materials have been considered and tested, although it is appreciated that many other materials may present feasible options for carriers.

A summary of the carrier materials tested are provided in the table below:

| Type | Sample No | Product | MTX g/ltr | Ag | Description |
|---|---|---|---|---|---|
| Cotton 100% | 1 | Zurga | 0 | 0 | |
| Cotton 50% Polyester 50% | 2 | Zurga | 15 | 3 | |
| Cotton 100% | 3 | Zurga | 7.5 | 1.5 | |
| Cotton 100% | 4 | Zurga | 5 | 0.5 | |
| Cotton 100% | 5 | Zurga | 15 | 3 | |
| Cotton 50% Polyester 50% | 6 | Zurga | 5 | 0.5 | |

| | Product | Manufacturer | Type |
|---|---|---|---|
| Existing Masks | | | |
| Covaflu Mask FFP3 | 7 | Clinova | PF |
| Oxypura face mask | 8 | Industrial Reg. | Puritas | Carbon |
| Oxypura face mask | 9 | Industrial Sup. | Puritas | |
| Oxypura face mask | 10 | Domestic | Puritas | |
| Dasheng Face Masks | | | |
| DS DAC4X-F | 11 | | |
| DAC4M-F | 12 | | |
| DS DAC4-OF | 13 | | |
| DS DAC4R-F | 14 | | |
| Activated Carbon Cloth | | | |
| FM10 - Zorflex VB | 15 | | Chemviron |
| FM10 T230 - Zorflex VB+ | 16 | | Chemviron |
| FM 10 Char washed | 17 | | Chemviron |
| FM10 Rayon, partcodeR163 | 18 | | Chemviron |
| Nonwoven Carbon Veil | | | |
| Optimat 20301A | 19 | | TFP |
| Optimat 20301A | 20 | | TFP |
| Activated Carbon Granules | | | |
| Envirocarb207C 4X8US | 21 | | Chemviron |
| Aquacarb207C 12X30US | 22 | | Chemviron |

MTX (CHT, Germany) is a carbohydrate polymer, which behaves as a reactive organic-inorganic binder system, based on a nanotechnolgical sol gel process. The MTX is thought to functionalise the cotton textile surface and can be used in combination with other textile surfaces. When used in combination with iSys Ag, the surface finish is provided with an anti-microbial effect, since the Ag is permanently embedded in the MIX binder matrix.

Other carbohydrate polymers or other carbohydrates may be as effective as MTX.

Pathogen-Binding Components

The Role of Sialic Acid Against Pathogens

Sialic acid is a generic term used for a family of 9-carbon monosaccharides structurally deduced from neuraminic acid. Currently more than 50 different sialic acids variants have been identified in the nature.

Viral infections are initiated by specific attachment of a virus particle to receptors at the surface of the host cells. For many viruses, these receptors are glycans that are linked to either a protein or a lipid. Glycans terminating in sialic acid and its derivatives serve as receptors for a large number of viruses, including several human pathogens.

Bacterial infections incorporate sialic acid into their own cell surface features, although this characteristic is usually limited to those that live in association with higher animals (deuterostomes). The sialic acid-decorated cell surfaces of a bacterium enable them to disguise themselves and resist a host's innate immune response and so, sialic acid and its derivatives have been identified as useful target components for the purpose of the invention.

Sialic Acid and its Derivatives as Pathogen-Binding Components

In view of the above observations sialic acid and its derivatives have been identified as useful pathogen-binding components, particularly in the case of sialic acid-binding pathogens, such as viruses.

Oligosaccharides as Pathogen-Binding Components

Sialic acids and its derivatives are not readily attached to many components. However, they do tend to form conjugates with oligosaccharides with relative ease.

Accordingly, oligosaccharides with an affinity for sialic acid and its derivatives have been identified as useful pathogen-binding components for the purpose of the invention, particularly in the case of sialic acid-expressing pathogens, such as bacteria.

Binding Intermediates

Since sialic acids and its derivatives tend to form conjugates with oligosaccharides with relative ease, oligosaccharides with an affinity for sialic acid and its derivatives have been identified as useful binding intermediates in the case of a sialic acid pathogen-binding component.

Oligosaccharides in turn are often a key component of glycoproteins, which makes a protein component a useful binding intermediate in the case of an oligosaccharide pathogen-binding component.

Pathogen-Binding Conjugates

Pathogen binding conjugates for the purpose of the invention relate to a conjugation of a sialic acid or derivative thereof (pathogen-binding component) and the oligosaccharide binding intermediate.

Pathogen-Binding Constructs

Pathogen binding constructs for the purpose of the invention relate to an attachment of an oligosaccharide pathogen-binding component and a protein binding intermediate, often referred to as a glycoprotein.

Fetuins are blood glycoprotein that is made in the liver and secreted into the bloodstream. Fetuin is more abundant in foetal blood and foetal calf serum contains a good source as is bovine milk. It is a heavily glycosylated protein isolated from foetal calf serum holding up to 8.7% of sialic acid on its surface, making it a useful pathogen-binding construct.

Accordingly, the following (glycosylated) glycoproteins have been identified as suitable pathogen-binding constructs:

Fetuin from bovine serum (F2379, lyophilized powder);
asialofetuin from bovine milk and foetal calf serum (A4781, Type I);
albumin from bovine serum (A7906, BSA, lyophilized powder); and
Lactoferrin (LF) from bovine colostrum (L4765).

Generally, bovine milk contains 30-35 grams of proteins per liter of which about 80% is arranged in casein micelles. There are four different types of casein proteins: αs1-, αs2-, β-, and κ-caseins. Milk also contains dozens of other types of proteins beside the caseins, including enzymes. These other proteins are more water-soluble than the caseins since they do not form larger structures. Since these proteins remain suspended in the whey left behind when the caseins coagulate into curds, they are collectively known as whey proteins. Whey proteins make up approximately 20% of the protein in milk by weight. β-lactoglobulin is the most common whey protein (about 10%). The remaining protein components are α-lactalbumin (about 2%) serum albumin (about 1%) immunoglobulins (about 2%) and other proteins (about 5%).

Accordingly, the following milk glycoproteins have also been identified as suitable pathogen-binding constructs in addition to the above identified glycoproteins:

GMP (a sialic acid containing glycomacropeptide fragment of κ-casein 106Met-169Val);
α-casein from bovine milk (C6780, lyophilized powder);
β-casein from bovine milk (C6905, BioUltra);
κ-casein from bovine milk (C0406, lyophilized powder);
α-lactalbumin from bovine milk (L5385, Type I, lyophilized powder); and
β-lactoglobulin from bovine milk (L3908, lyophilized powder).

Advantageously, the minor glycoproteins can also be extracted from bovine milk using various chromatography methods such as ion exchange chromatography, column chromatography, Reversed-Phase High-Performance Liquid Chromatography, cation exchange chromatography. By extracting the glycoproteins in this manner would not require them to be lyophilised and they can be utilised directly in liquid form.

Overview of the Method

The method of making an anti-pathogen device generally comprises the following steps:
a) providing a carrier;
b) providing a pathogen-binding component;
c) providing a binding intermediate;
d) attaching the pathogen-binding component to the binding intermediate to form a pathogen-binding construct; and
e) attaching the construct to the carrier.

The main aim of the method is to arrive at a device that can capture viruses or bacteria/other pathogens by providing a pathogen-binding component and using the carrier to retain the pathogen, whilst delivering other factors or components (on the carrier) to the pathogen that might neutralise or kill the pathogen.

PROTOCOL A: Binding the Pathogen-Binding Construct to a Cloth Carrier

In the following method, the construct (binding intermediate and pathogen-binding component) is provided in the form of a glycoprotein.

1. Glycoprotein solutions using one of the selected glycoproteins were prepared by dissolving solid protein in water at room temperature.
2. A carrier was placed in a first disposable petri dish and weighed.
3. 1 of glycoprotein solution (e.g. 1 mg/mL) was added to the first petri dish.
4. The first petri dish was covered with a lid and placed in an incubator at room temperature.
5. After 40 minutes to 1 hour the first petri dish was removed.
6. The carrier was removed from the glycoprotein solution and placed in a clean second petri dish.
7. The second petri dish was placed in an oven at 55° C.-60° C. for 2 hours until the carrier was dry.
8. The second petri dish was than placed in a desiccator under vacuum for 30 minutes.

PROTOCOL B: Binding the Pathogen-Binding Construct to a Granule Carrier

In the following method, the construct (binding intermediate and pathogen-binding component) is provided in the form of a glycoprotein.

1. Glycoprotein solutions using one of the selected glycoproteins were prepared by dissolving solid protein in water at room temperature.
2. 200 mg of absorbent carrier granules were weighed into a fritted column
3. 1 mg/mL of the glycoprotein solution was added into the column.
4. The column was left to incubate at room temperature.
5. After 40 minutes to 1 hour the column was removed.
6. The granules were filtered out of the solution and the solution was retained.
7. The granules were placed in an oven at 55° C.-60° C. for 2 hours until the granules were dry.
8. The granules were then placed in a desiccator under vacuum for 30 minutes.

PROTOCOL C: Binding the Pathogen-Binding Construct to a Carrier by Alternative Spraying This method of binding was only tested for cloth carriers.

Again, the construct (binding intermediate and pathogen-binding component) was provided in the form of a glycoprotein.

1. Different concentrations (1 mg/mL, 5 mg/mL, and 10 mg/mL) of glycoprotein solutions using one of the selected glycoproteins were prepared by dissolving solid protein in water at room temperature
2. A first carbon cloth sample was placed in a spraying chamber.
3. A 1 mg/mL glycoprotein solution was applied onto the cloth by 6 shots (1 shot/sec) using a spray-gun.
4. The cloth was removed from spraying chamber and placed in a clean petri dish.
5. Steps 3 and 4 were repeated on second and third cloth samples with a 5 mg/mL glycoprotein solution and a 10 mg/mL glycoprotein solution respectively.
6. The three petri dishes were placed in an oven at 55° C.-60° C. for 2 hours until the cloth samples were dry
7. The three petri dishes were then placed in a desiccator for 30 minutes.

PROTOCOL D: Testing Glycoprotein Adsorbance to the Carrier

This was tested by assessing the amount of glycoprotein that remains in the solutions from Protocols A and B, from which it can be derived how much of the glycoprotein had been captured or adsorbed by the carrier.

With Protocol C, no solution was retrieved due to the spray method of application and so, Protocol C could not be subject to this testing.

From Protocol A, the solution from the first petri dish after step 6 was tested.

From Protocol B, the solution from step 6 was subject to centrifugation at 4000 rpm for 10 min, to remove carbon debris and the filtrate was tested.

The glycoprotein solutions were used for protein concentration measurements detected by UV absorbance of the solution.

In order to get accurate concentration measurements, for every experiment, a calibration run is conducted. It has advantageously been observed that for all tested glycoproteins, there was a linear relationship between UV absorbance at 280 nm and the concentration of the glycoprotein in the solution when the concentration is within the range of 0.2-1.0 mg/mL (shown in FIG. 1).

The UV absorbance readings were taken by the TECAN Infinite M200 plate reader.

Adsorbance of Different Carriers Using Protocols A and B

Sample carriers identified previously as Samples 1-6 and Samples 15-18 were subjected to the method of Protocol A and Samples 18-19 were subjected to the method of Protocol B using the glycoprotein fetuin.

Group 1 Samples 1-6 (Product Zurga) represented various cotton and cotton-polyester mixes impregnated with varying amounts of MTX and silver nanoparticles.

Group 2 Samples 15-17 represented various carbon cloth samples from Chemviron and Sample 18 represented a Rayon product from Chemviron.

Group 3 Samples 19-20 represented nonwoven carbon veils from TFP.

Figure 2:
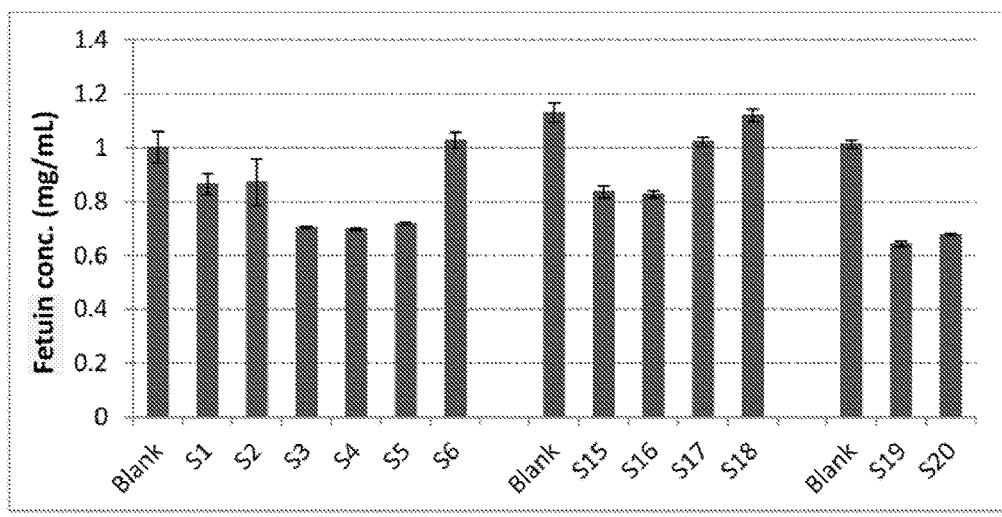
FIG. 2 is a graphical representation of the fetuin adsorption capability of various cloth carriers.

The results of the UV absorbance readings are shown in FIG. 2. Group 1, samples 3, 4 and 5 (100% cotton samples impregnated with between 5 and 15 g/ltr MTX) appeared to have the greatest take-up rate of fetuin, leaving the smallest amounts behind in the remaining solution. The worst take-up rate was observed by Sample 6 (cotton polyester blend with 5 g/it MTX).

The Group 2 samples (the activated charcoal cloths) showed that samples 15 and 16 had the best take-up rate of fetuin, with sample 18 (Rayon) performing the worst with very little take-up.

Group 3 samples (activated charcoal granules) demonstrated excellent take up of fetuin in both cases.

The results suggest that activated charcoal, cotton impregnated with MTX and activated carbon granules are suitable as carriers.

The results also suggest that the 'dipping' method of Protocol A for applying glycoproteins onto a cloth carrier can be used in production.

Adsorbance of Different Glycoproteins by Carbon Cloth Carrier Using Protocol A

The following glycoproteins were used in the method of Protocol A to prepare the glycoprotein solutions in Step 1 for adsorbance on to a 2×2 cm² carbon cloth carrier:

| Fetuin | β Casein | α-Lactalbumin |
| Asialofetuin | κ-Casein | β-Lactoglobulin |
| α-Casein | Lactoferrin | Albumin |

The results of the UV absorbance readings are shown in FIG. 3.

The cloth sample appeared to have the greatest take-up rate of β Casein, with fetuin and asialofetuin also having good adsorption results.

The cloth samples showed some adsorbance of α-Casein, κ-Casein and Lactoferrin, with α-Lactalbumin, β-Lactoglobulin and Albumin showing disappointing results.

PROTOCOL E: Testing the Binding Efficacy of the Anti-Pathogen Devices

In order to assess the efficacy of the pathogen-binding ability of the devices, an assay was designed and performed on the devices.

The assay relied upon the discovery that plant lectins are able to bind sialic acid and therefore, the presence and amount of bound lectins indicates the presence and amount of sialylated proteins, e.g. glycoproteins. These lectins can serve as suitable influenza haemagglutinin (HA) mimics, instead of having to run tests with HA proteins.

Of the plant lectins, primarily wheat germ agglutinin (WGA) and *sambucus nigra* (SNA) have been identified as suitable proteins for mimicking the binding of influenza HA.

Although WGA binds specifically to 2-acetamido-2-deoxy-D-glucose (GlcNAc) and its β-(1,4)-linked oligomers, the interactions of WGA with sialic acid were also observed.

WGA appears to have particularly strong affinity for α2,3-bound sialic acid (Kronis & Carver 1982; Iskratsch et al. 2009).

*Sambucus nigra* lectin (SNA, elderberry lectin) is the lectin of choice for examining the presence of terminal α-2,6-sialic acid in many biomedical and biotechnological applications. Although SNA was first reported to be a galactose-specific lectin, is has later been found to bind preferably to sialylated oligosaccharides. (Shibuyas et al. 1987; Haseley et al. 1999).

The presence of lectins in a solution can be identified by fluorescence. Accordingly, WGA and SNA assays have been performed to assess the effectiveness of devices made according to the invention, by detecting the amount of WGA and SNA remaining in the solution (after binding) by fluorescence.

Materials

The testing methods used the following materials:
  lectin from *Triticum Vulgaris*, wheat (L4895. WGA-FITC conjugate, lyophilized powder);
  phosphate buffered saline (P4417, PBS tablet) purchased from Sigma-Aldrich;
  Fluorescein labelled *sambucus nigra* lectin (FL-1301, SNA-FITC, EBL-FITC) purchased from Vector Laboratories; and
  Devices made according to the invention including:
    Fetuin-adsorbed carbon cloth
    β Casein-adsorbed carbon cloth
    α-Lactalbumin-adsorbed carbon cloth
    Asialofetuin-adsorbed carbon cloth
    κ-Casein-adsorbed carbon cloth
    β-Lactoglobulin-adsorbed carbon cloth
    α-Casein-adsorbed carbon cloth
    Lactoferrin-adsorbed carbon cloth
    Albumin-adsorbed carbon cloth.

Method

Figure 5:
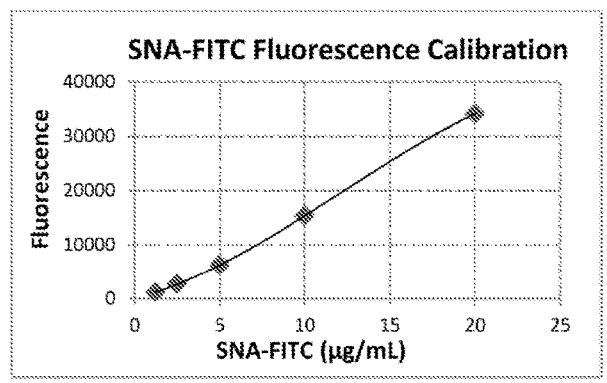
FIG. 5 is a graphical representation of the relationship between SNA-FITC (tag) concentration and fluorescence (calibration)

1. Lectin stock solutions were prepared by:
   a. dissolving 5 mg/mL of solid WGA-FITC in phosphate buffered saline (PBS) at room temperature;
   b. dissolving 2 mg/mL of solid SNA-FITC in phosphate buffered saline (PBS) at room temperature;
2. Each lectin stock solution was kept in the dark at 4° C.
3. Phosphate buffered saline (PBS) was prepared by following manufacturer recommendation of one tablet dissolved in 200 mL of deionized water to obtain 0.01 M phosphate buffer, 0.0027 M potassium chloride and 0.137 M sodium chloride, pH 7.4, at 25° C.;
4. The following lectin solution concentrations were prepared from the WGA and SNA stock solutions by diluting the stock solutions with PBS:
   a. A 20 μg/ml WGA solution;
   b. A 10 μg/ml SNA solution;
5. One sample (2×2 cm) of each device was each placed in a first disposable Eppendorf Tube and 1.0 mL of WGA lectin solution from step 4 was added.
6. Another sample (2×2 cm) of each device was each placed in a second disposable Eppendorf Tube and 1.0 mL of SNA lectin solution from step 4 was added.
7. The ETs were closed and left to incubate for 3 hours at 37° C.
8. The devices were removed from the lectin solutions and the remaining solutions were subject to fluorescence measurements by TECAN Infinite M200 plate reader As fluorescence of the lectin solution is dependent on the concentration of the fluorescein isothiocyanate (FITC) a calibration was performed in PBS buffer with values 488 nm for excitation and 530 nm for emission by TECAN instrument for all experiments. The fluorescence values obtained for both WGA-FITC and SNA-FITC showed high accuracy of this method as linear relationship between fluorescence and concentration in the range 5-25 μg/mL was observed. The linear relationship for both WGA-FITC and SNA-FITC can be seen in FIGS. 4 and 5, respectively.

Figure 6A:
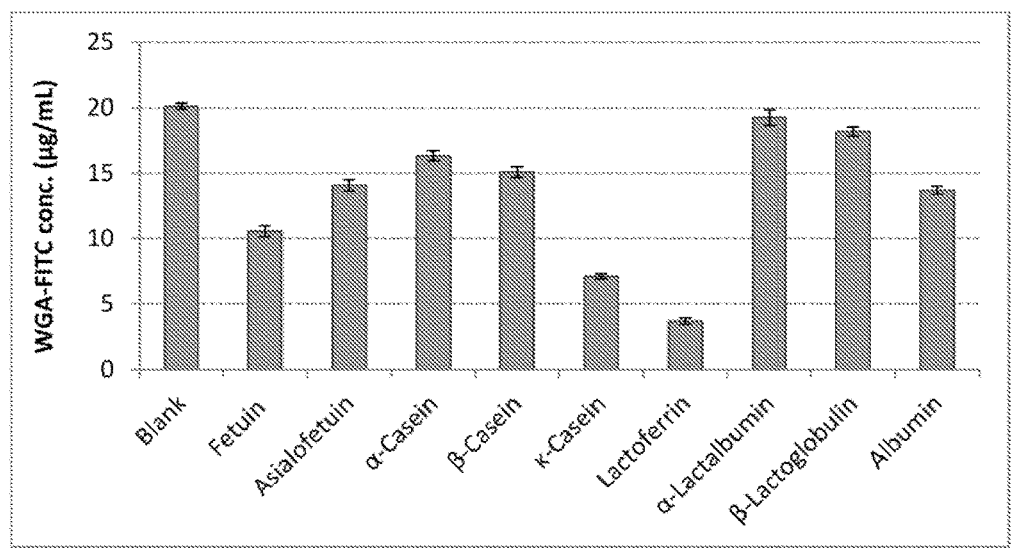
FIG. 6a is a graphical representation of the concentrations of WGA-FITC (tag) remaining in solution following exposure to carrier cloths made according to the present invention.
Figure 6B:
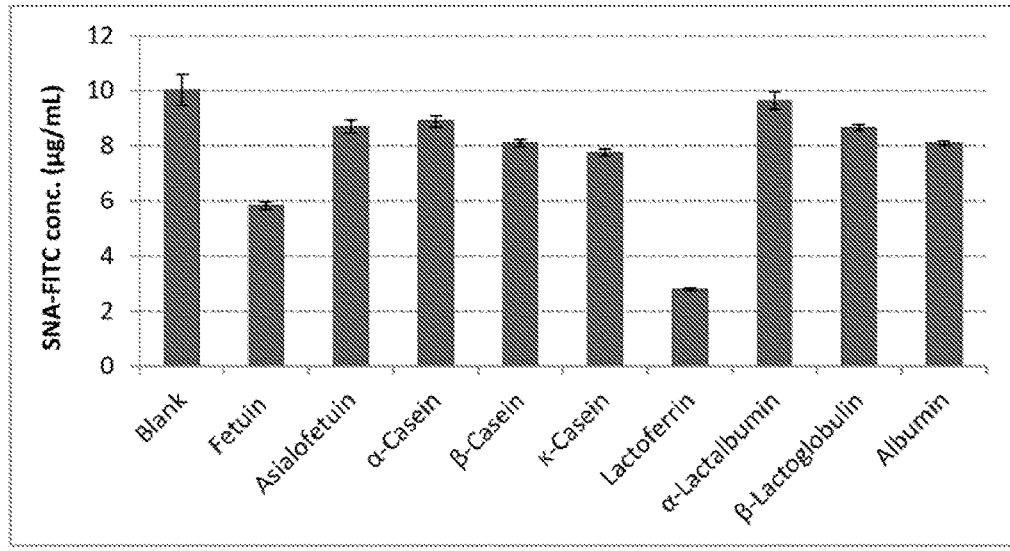
FIG. 6b is a graphical representation of the concentrations of SNA-FITC (tag) remaining in solution following exposure to carrier cloths made according to the present invention.

Binding of Lectins to Different Glycoproteins by Carbon Cloth Carrier Using Protocol A The results of the assays are shown in FIGS. 6a and 6b.

The concentration of the lectin in the solution before binding is marked as "Blank", others measured concentrations are marked with the name of tested protein. Columns showing lower concentration values suggest stronger lectin binding what could indicate better performance also for virus binding in the viral filtration devices.

From the obtained results it can be concluded that all tested glycoproteins had a lectin binding activity to greater or lesser extents. The results did not necessarily reflect the results of the glycoprotein adsorbance results, which was interesting.

Fetuin, κ-casein and lactoferrin were found to have the best lectin binding activity, with lower concentrations of the lectins being left in the solutions.

The strongest lectin binding activity was observed with a lactoferrin device.

Confirming Specific Binding of the Lectin onto Fetuin

To confirm specific binding of the lectin onto fetuin a method based on fluorescence microscopy has been used. Fluorescence of WGA-FITC was observed on carbon cloth (Sample 15) impregnated with fetuin, then dipped into lectin solution and washed with PBS buffer. The fluorescence microscopy images are not shown, but it was noted that prior to washing in PBS buffer, the carbon cloth showed a high degree of fluorescence, which was diminished, but still observed post-washing.

On carbon cloth impregnated with asialofetuin, dipped into lectin solution and washed with PBS buffer, fluorescence of WGA-FITC was not observed. This is to be expected as asialofetuin is desialylated and so the WGA-FITC had no binding target.

Figure 7:
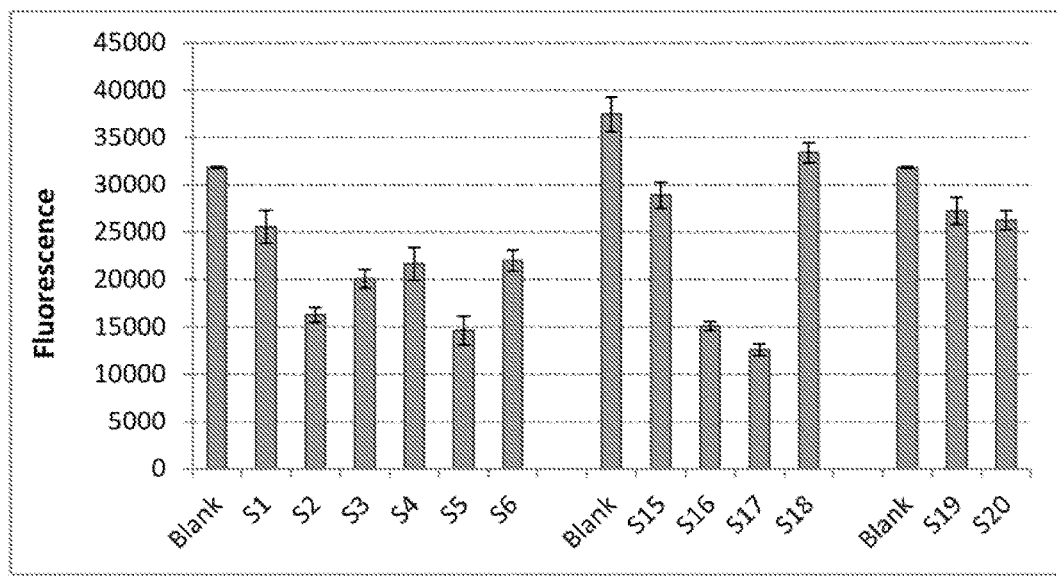
FIG. 7 is a graphical representation of the WGA-FITC (tag) fluorescence of solutions following exposure to carrier cloths made according to the present invention.

Binding of Lectins to Devices Comprising Different Cloth Carriers Using Protocol A The lectin assay was performed on devices comprising different carrier materials adsorbed with fetuin using WGA only. The results of the assays are shown in FIG. 7.

The concentration of the lectin in the solution before binding is marked as "Blank", others measured concentrations are marked with the Sample number. Columns showing lower concentration values suggest stronger lectin binding what could indicate better performance also for virus binding in the viral filtration devices.

Group 1 Samples 1-6 (Product Zurga) represented various cotton and cotton-polyester mixes impregnated with varying amounts of MTX and silver nanoparticles.

Group 2 Samples 15-17 represented various carbon cloth samples from Chemviron and Sample 18 represented a Rayon product from Chemviron.

Group 3 Samples 19-20 represented nonwoven carbon veils from TFP.

Generally, from the obtained results all tested fabrics appear to adsorb fetuin from the solution, but at different levels.

From Group 1, samples 2 and 5 appeared to have the best lectin binding activity (Cotton/Polyester mix and Cotton both with 15 g/ltr MTX), but on the whole all samples demonstrated a good binding activity.

From Group 2, samples 16 and 17 stood out as being exceptional (Zorflex VB+ and Char washed), with all samples demonstrating an acceptable-good binding activity. In the case of sample 17, there is a significant manufacture saving since the rayon base material only has to be subjected to a single furnace step, therefore cutting down manufacturing time and therefore, cost of the carrier.

Both of the Group 3 samples demonstrated some lectin-binding activity.

The cotton and activated charcoal carrier show promising results with fetuin.

Binding of Lectins to Devices Comprising Different Granule Carriers Using Protocol B To test the possibility of using carbon granules as a carrier an initial set of experiments were conducted using glycoprotein fetuin.

Activated carbon Norit® and activated carbon granules from Chemviron (Samples and 22 were tested for lectin binding activity.

The granules were subject to Protocol B using fetuin as the glycoprotein.

To examine lectin binding onto modified granules, 2 mL of lectin solution in PBS buffer (20 µg/mL for WGA-FITC and 10 µg/mL for SNA-FITC) was passed through the column at flow rate 2 mL/min at room temperature.

In order to establish how much of the lectin had bound to the modified granules, the amount of lectin remaining in the filtrate was measured and used to establish how much was retained by the modified granules.

The filtrates were collected and analysed by fluorescence measurement.

The results are shown in FIGS. 8a and 8b.

From the results obtained it can be concluded that all the activated carbon granule samples adsorb fetuin and lectins albeit in different amounts. Non-specific binding was observed in the negative control (when no carbon was included) by the reduction of both the measured amounts of free fetuin and the fluorescence in the lectin binding assay, this probably arose from the binding/retention of the proteins within the frit of the column.

Greater reduction in free fetuin in the NORIT sample shows that there is binding of protein to the carbon. The other two samples show less fetuin binding, the same is true for the lectin binding assay with NORIT performing the best whilst the two samples (21 and 22) showing only minor binding (when compared to the negative control). The unspecific binding directly onto activated carbon or fluorescence quenching needs to be further examined. Furthermore, material which will be used for the adsorption or covalent attachment of fetuin and consecutive virus binding from flowing liquids should be probably more rigid (resist mechanical splitting) and have greater adsorption surface area.

In comparison to carbon granules, the possibility of using fetuin modified carbon cloth for viral particles removing directly from flowing liquids was also examined. To adsorb fetuin onto the carbon cloth the material (Sample 16) was weighed into fritted PROTOCOL F: Specific Example—Capture of the Human Influenza Virus by Fetuin Modified Carbon Cloth In order to test if the lectin assay indications were a good reflection of whether the devices of the present invention would be efficient in trapping flu virus particles, an experiment using aerosolised flu virus particles passing through fetuin modified carbon cloth was designed and tested.

Apparatus

A schematic representation of the apparatus is shown in FIG. 9.

Materials

Influenza virus strain A/England/195/2009 (H1N1)

Zorflex VB Carbon Cloth samples (circles Ø 20 mm, 67-70 mg, In-line Pall Filter Holders)

Method

1. An in-line filter holder (3) with four independent ports was loaded as follows:
   a) empty filter holder
   b) neat (unmodified) carbon cloth (not the invention)
   c) fetuin-modified carbon cloth containing 0.6 mg fetuin/100 mg carbon cloth
   d) fetuin-modified carbon cloth containing 2.5 mg fetuin/100 mg carbon cloth
2. A 500 µl of $1.275 \times 10^7$ pfu/ml sample of the influenza virus in PBS buffer was injected into a nebuliser (1) on the top of the apparatus.
3. Aerosol-containing viral particles are then formed inside a chamber (2) and are sucked through the in-line filter holder (3) at a flow rate of 2.5 l/min (each sample) for 10 min controlled by an airflow controller (4).
4. The airflows exiting the filter holder (3), having been 'filtered' by the devices in ports 2-4, enter separate air samplers (5) filled with 50 ml of PBS on ice to collect the resulting filtered phase for viral analysis.
5. The bio-sampler content was used in a plaque assay to determine the virus amount.

To minimise handling and preparative errors, the experiment was repeated after cleaning and disinfecting the apparatus. Results from both runs were compared and are summarised in FIG. 10.

Considering the amount of virus used for each run ($1.275 \times 10^7$ for 4 samples), approximately a 40 fold reduction in virus particles was observed in Sample a (without a carbon cloth filter). The unmodified carbon cloth (sample b) appeared to be able to capture approximately 90% of the viruses. With fetuin devices according to the invention (samples c and d), the amounts of detected viruses were on the limit of detection: with sample c (containing 0.6 mg fetuin/100 mg carbon cloth) no virus was detected in the filtrate, whilst in sample d (containing 2.5 mg fetuin/100 mg carbon cloth), 625 viral particles were detected in the whole sample which represents above 99% efficiency.

The following formula was used to calculate overall percentual depletion:

If you have one process with A % depletion and a second process with B % depletion, then one would expect the overall yield of C % depletion of virus to be:

$$c = 100 - [(100-a) \times (100-b)]/100$$

For example, if one process reduces the virus count by a=20% and one by b=90%, the overall efficiency of removal of virus $c = 100 - [(100-20) \times (100-90)]/100\% = 92\%$ Following on from the proposed equation, the depletion of viruses from airflow as it was experimentally performed was:

$A = 100 - 7875 \times 100/77500 = 89.84\%$ (depletion observed using carbon cloth)

$B = 100 - 625 \times 100/7875 = 92.06\%$ (depletion observed when adding fetuin)

$C = 100 - [(100-89.84) \times (100-92.06)]/100 = 99.2\%$ (overall depletion observed using fetuin and carbon cloth)

PROTOCOL G: Testing Longevity of the Devices According to the Invention

To ascertain the consistency of the virus binding activity of devices according to the invention over a period of time (stability testing), lectin binding activity has been tested on a fetuin adsorbed carbon cloth after various periods of time.

All experiments were performed with Zorflex VB carbon cloth (Sample 15) with ca. 6×6 cm square samples using 1 mL of fetuin solution (fetuin concentration 1 mg/mL) per 100 mg carbon cloth and subjected to Protocol A.

As time course of fetuin binding onto carbon cloth revealed that it takes ca. 20 min to reach adsorption equilibrium at room temperature (see previous report), a minimum time of 40 min has been chosen for all longevity test experiments and all samples were checked for fetuin binding onto carbon cloth.

Dried samples of the devices were stored for:
1 week, 2 weeks, 1 month, 3 months and 5 months In addition to these five time periods, different samples were stored under different conditions:
at room temperature in an open container,
at room temperature in a closed container,
at room temperature in a closed container in inert atmosphere (under N2),
in a fridge at 4° C. in a closed container,
in a fridge at 4° C. in a closed container in inert atmosphere (under N2)

Each sample was then subjected to the lectin assay method steps of Protocol E.

However, to block unspecific binding of lectins directly onto carbon cloth, samples were dipped into bovine serum albumin (BSA) solution as a blocking protein prior to the lectin assay.

Figure 11:
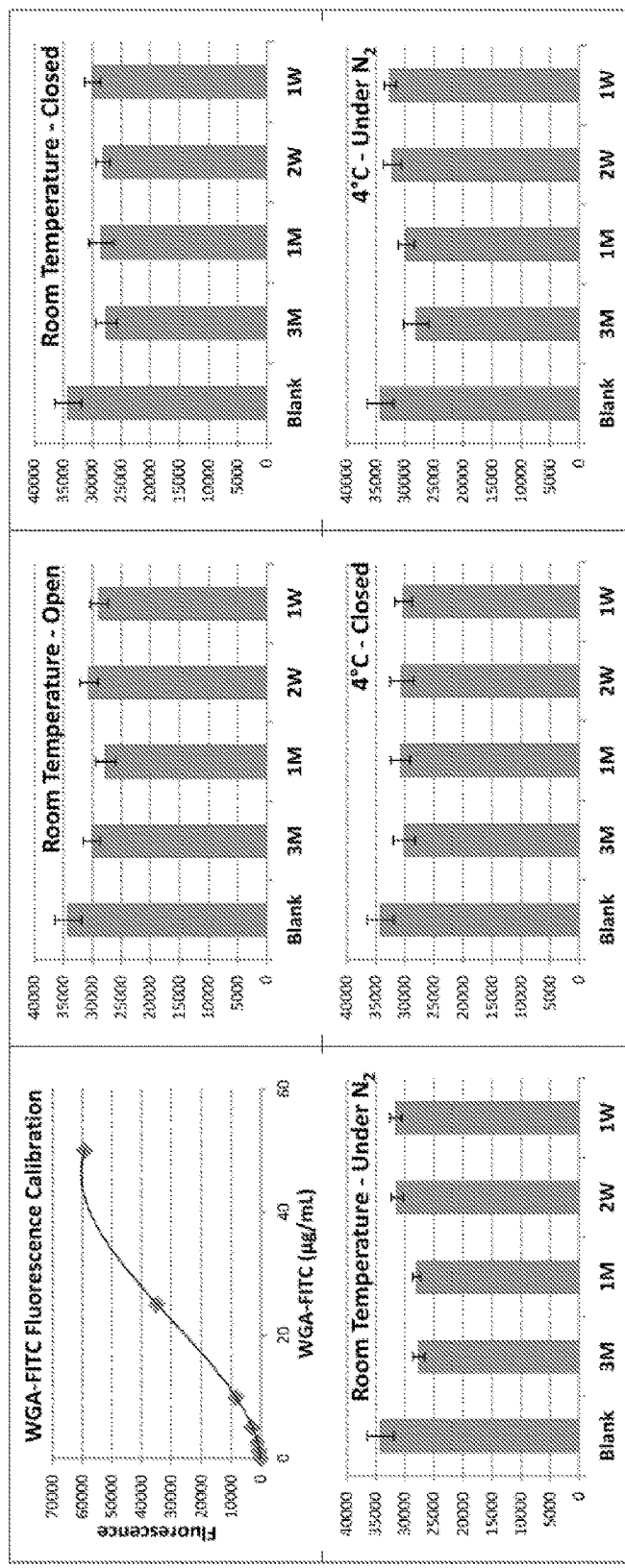
FIG. 11 shows a series of graphical representations demonstrating the WGA-FITC binding ability of a carbon cloth-fetuin device made according to the invention at various times following creation (longevity testing)
Figure 13:
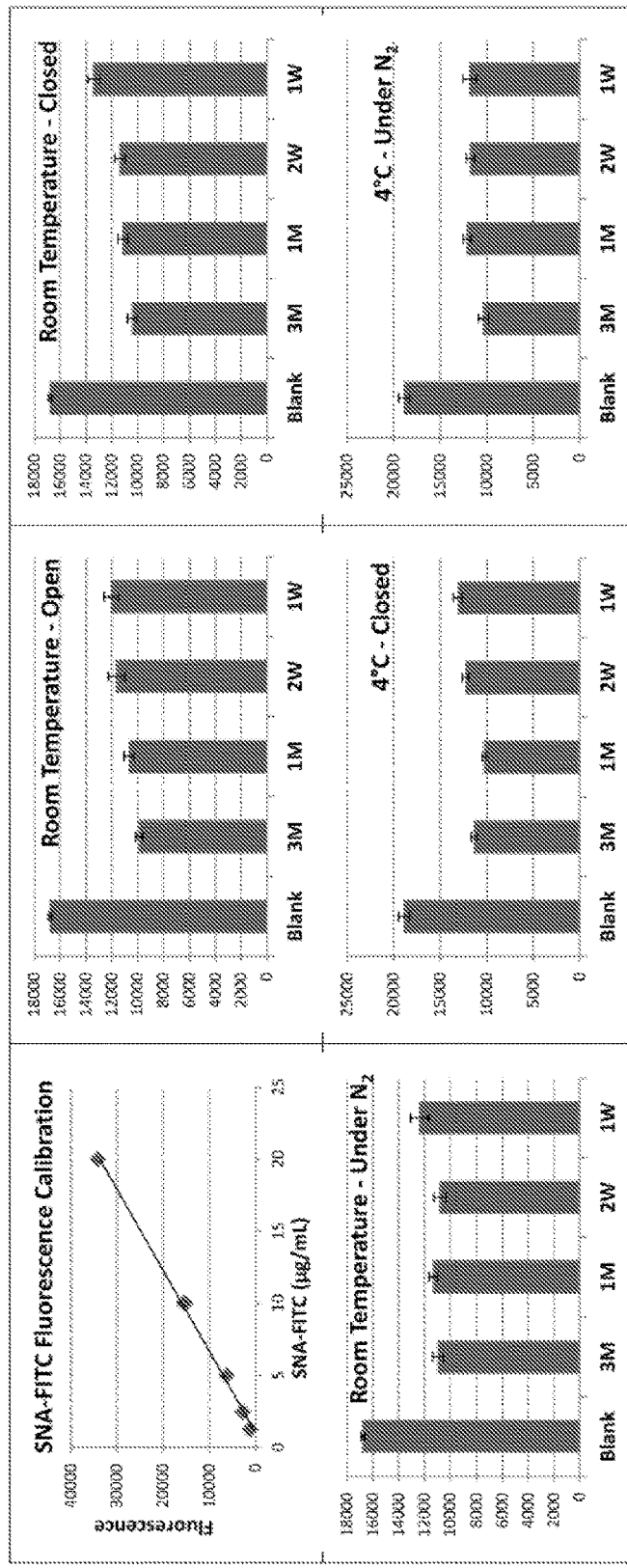
FIG. 13 shows a series of graphical representations demonstrating the SNA-FITC binding ability of a carbon cloth-fetuin device made according to the invention at various times and being kept under various conditions following creation (longevity testing)
Figure 14:
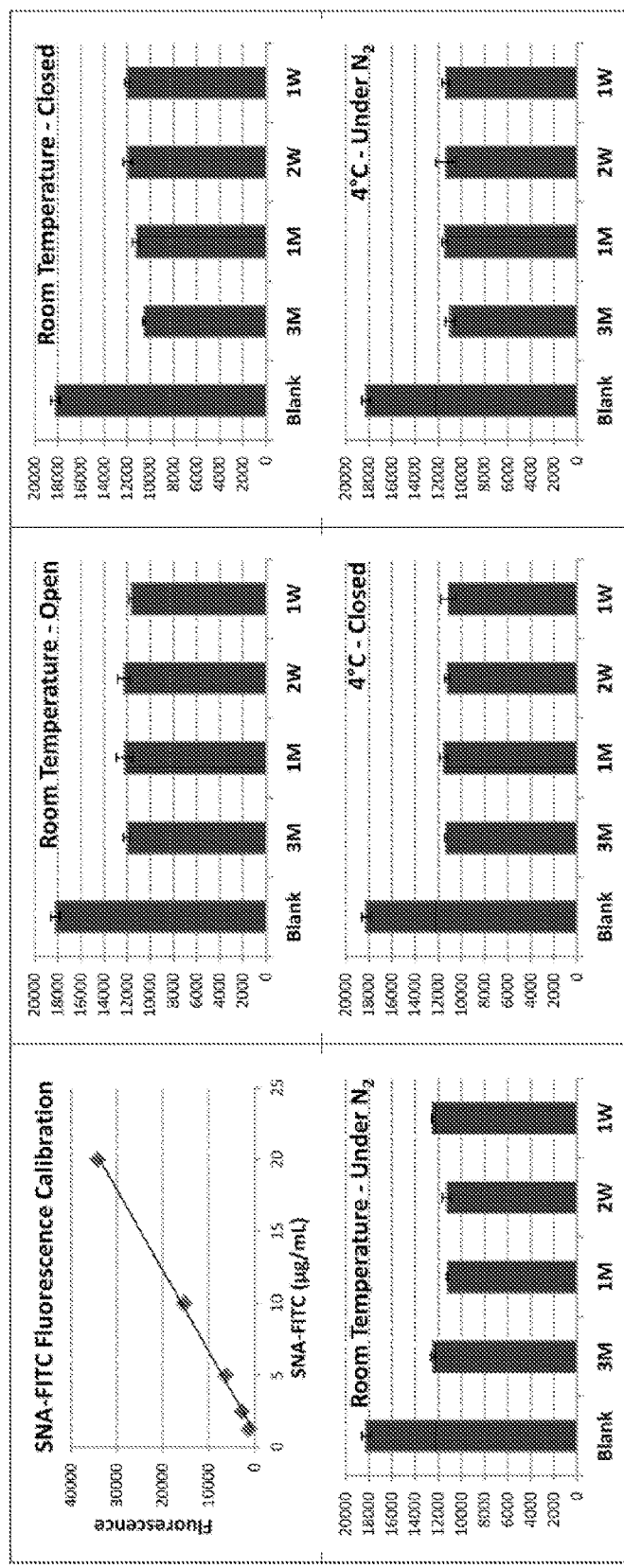
FIG. 14 shows a series of graphical representations demonstrating the SNA-FITC binding ability of a carbon cloth-fetuin device made according to the invention at various times and being kept under various conditions following creation (longevity testing) following treatment with BSA.

The obtained results are graphically depicted in FIGS. 11-16, with FIGS. 11 and 14 representing the 1 week to 3 month results and FIGS. 15 and 16 representing the later 5 month results.

Figure 12:
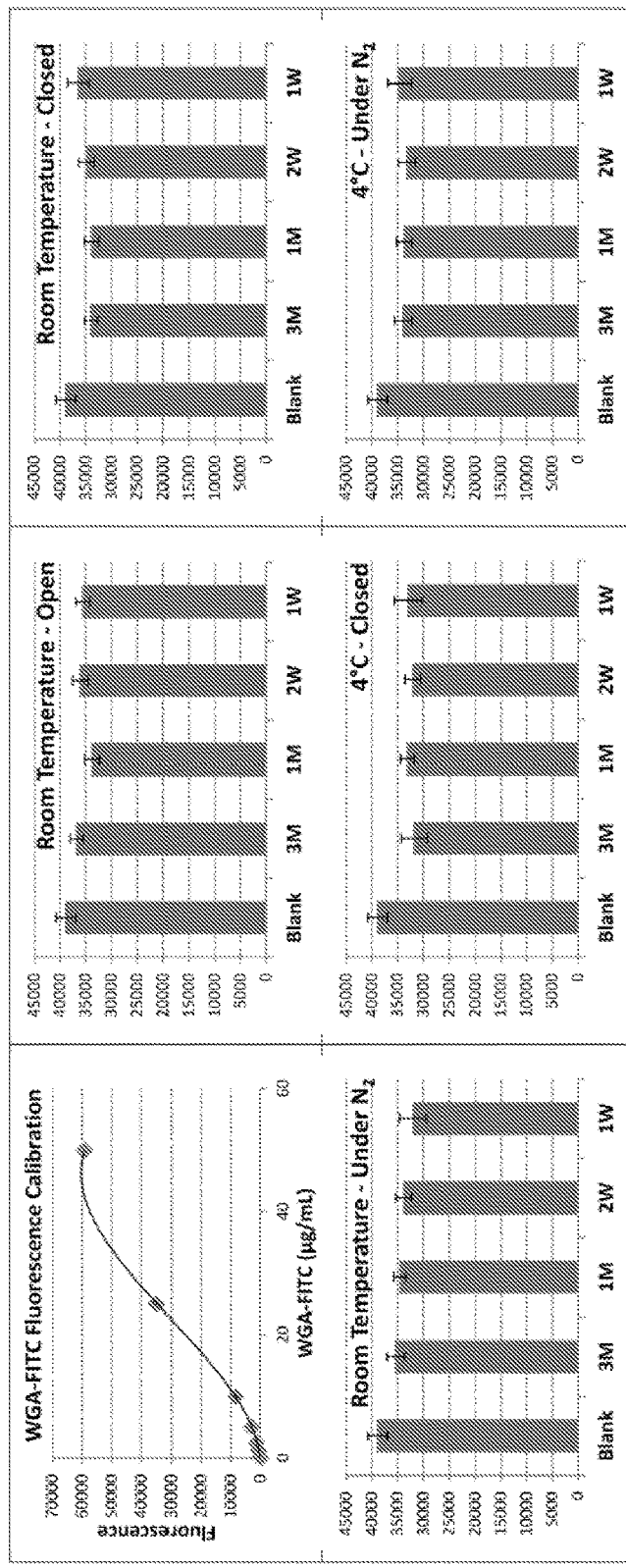
FIG. 12 shows a series of graphical representations demonstrating the WGA-FITC binding ability of a carbon cloth-fetuin device made according to the invention at various times and being kept under various conditions following creation (longevity testing) following treatment with BSA.

FIGS. 11, 12 and 15 represent WGA assays: FIG. 11 shows the WGA binding activity without BSA blocking and FIG. 12 shows the WGA binding activity with BSA blocking. FIG. 15 shows WGA binding activity without BSA blocking and with BSA blocking in side-by-side arrangement.

FIGS. 13, 14 and 16 represent SNA assays: FIG. 13 shows the SNA binding activity without BSA blocking and FIG. 14 shows the SNA binding activity with BSA blocking. FIG. 16 shows SNA binding activity without BSA blocking and with BSA blocking in side-by-side arrangement.

In each of the tests a fluorescence calibration was performed. For each of the tests, the initial concentration of the lectin in the solution before binding is marked as Blank. Other measured concentrations are marked with the storage time along the x axis. Columns showing lower fluorescence intensity values suggest stronger lectin binding which could indicate that the fetuin glycoprotein is still active and unmodified after the relevant time period.

Generally, from the obtained experimental results it can be inferred that the device appears to be stable, retaining its lectin binding activity even during long term storage under different storage conditions.

The anti-pathogen devices comprising fetuin on an activated carbon cloth appear therefore, to present as very good candidates for the production of viral filtration devices. It is anticipated that the other devices would present similar results.

PROTOCOL H: Suitability of the Product for Application to a Face Mask

For surgical masks that are not certified N95 Respirators, it is recommended to evaluate differential pressure or breathability. Differential Pressure (Delta-P) is the measured pressure drop across a surgical facemask material when gas flows through the filter (expressed in mm water/cm2). Pressure drop also relates to the breathability and comfort of the surgical mask. The lower Delta-P values (<3.0 mm) indicate easier breathing and decreased facial warmth beneath the mask. The higher the Delta-P, the more difficult the mask is to breathe through.

In order to test if the fetuin modified carbon cloth could be used as an additional extra layer for protection of for example such surgical face masks and do not affect the breathability pressure drop test has been designed and performed by Patricia Turnbull and Dr. Lande Liu at School of Chemical Engineering and Analytical Science at The University of Manchester.

The pressure drop test was performed with FM10 T230-Zorflex VB+ carbon cloth (Sample 16) with ca. 10×10 cm square samples using 1 mL of fetuin solution (fetuin concentration 1 mg/mL) per 100 mg carbon cloth for dipping. After dipping (soaking) the fetuin impregnated carbon cloth was dried at 55-60° C. for 2 h, followed by drying in a desiccator. Dried samples of the device have been tested. As negative control was used the unmodified carbon cloth as it was delivered.

Figure 17:
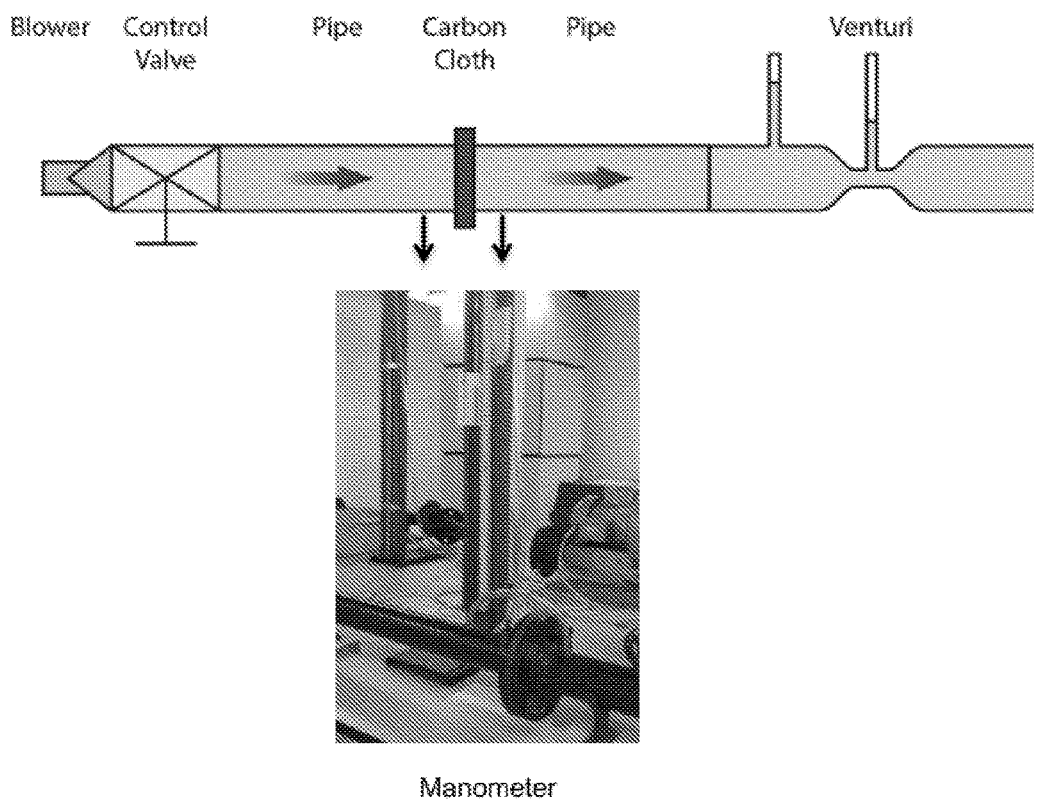
FIG. 17 is a schematic representation of an apparatus used for a pressure drop test on devices made according to the invention.

Schematic representation of the apparatus for pressure drop test is shown in FIG. 17 The carbon cloth (Sample 16) or fetuin modified carbon cloth was inserted in a middle of a pipe line. The airflow through the cloth was set up in a range 100-400 L/min. Pressure drop (Delta-P) was measured and calculated by monitoring of Delta-H by using Manometer and Venturi.

Pressure Drop can be also calculated using the Reynolds number (Re) determining laminar or turbulent flow.

$$Re = \frac{Dv\rho}{\mu}$$

Where D is the diameter of the pipe, v is the velocity of the fluid, ρ is the density of the fluid, and μ is the dynamic viscosity of the fluid. The measured and calculated values of Re are included in supporting information.

Figure 18:
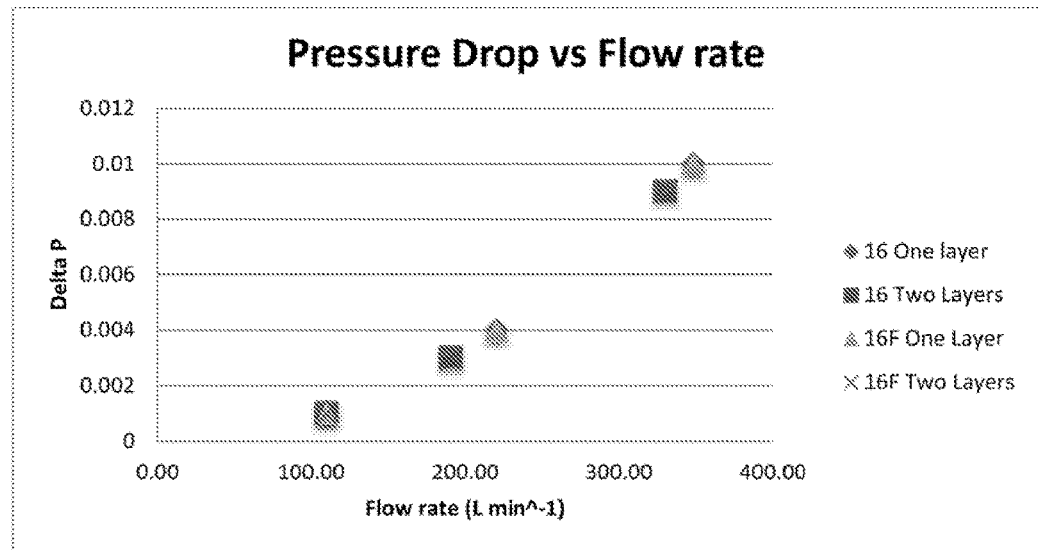
FIG. 18 is a graphical representation of the pressure drop versus flow rate when using a carbon cloth-fetuin device according to the invention.
Figure 19:
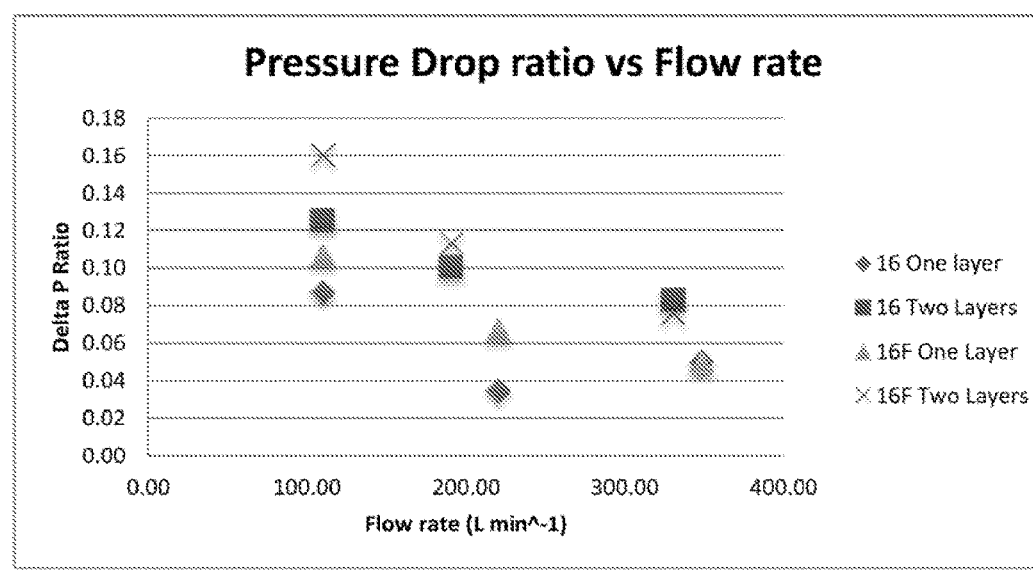
FIG. 19 is a graphical representation of the pressure drop versus flow rate using an unmodified carbon cloth control.

From the results obtained (FIGS. 18 and 19) it is clear that for the two materials the absolute pressure drop seems changing linearly with flow rate and two layers do not make too much difference. Also, the pressure head caused by the filter divided by the total head clearly shows that a lower flow rate would give a relatively higher friction loss across the cloth as expected. It also appears that the flow of the air in the pipe was in the laminar region according to the Reynolds numbers calculated.

In all performed experiments by using carbon cloth Sample 16, calculated pressure drop values were in range 0.02-1.68 mm/cm2. Two layers of cloth, shown the highest pressure drop 1.68 mm/cm2 at air flow rate 330 L/min. Modification of carbon cloth with fetuin had no impact on pressure drop or breathability, what suggests possibility to use the device as additional protection layer in face masks.

Remarks

It has been shown that a range of devices of the present invention show promising results for the binding of lectin and so, it is expected that, like the example of fetuin modified carbon cloth, that the anti-pathogen devices of the present invention could be used to effectively trap and neutralise viruses.

Specific embodiments include use of the anti-pathogen device as a filter, for example a filter in an article such as a facemask, an air conditioning unit, or a blood filtration device (such as a hemofilter). Use as a facemask is specifically envisaged.

When used as a hemofilter it could be used as part of a dialysis apparatus, or as an external filter through which the heart itself pumps blood.

The anti-pathogen device is used in air conditioning units, it can for example be used in vehicles such as cars or aircraft (for example in the form of granules or powder to be placed in pipes of the air conditioning unit). HEPA filters are currently used in aircraft, however these can still transmit viruses when they become wet. Additionally, the anti-pathogen device could be used to make commercial/household/medical items suitable for use as furnishings (such as curtains), surface coverings (such as tablecloths), or body coverings (such as gloves), to absorb viruses in the home, commercial or medical environment, or even to make cloths for the wiping of potentially virus-infected surfaces.

Further specific embodiments in which lactoferrin as a binding intermediate is attached to a (e.g. woven or non-woven) cotton substrate (or like carrier) using a carbohydrate binder such as MTX, as set out above, or even better, using iSys LTX (CHT, Germany) in a similar fashion, include the following:

Wound dressings.

These could utilise the anti-bacterial, healing properties and immune response modulation of lactoferrin.

Antibiotic Socks

Lactoferrin would be present when the skin is being damaged. Generally diabetics have a compromised immune system due to poor circulation particularly in the foot. Normal wound healing function to be restored using lactoferrin.

Mastitis Cups

The antiviral antibacterial and antifungal properties of lactoferrin would be used on the bovine teat to inhibit the access of pathogen into the teat canal when it is open after milking.

Facemasks—Filtration.

These would utilise the anti-viral and anti-bacterial properties of lactoferrin, or indeed an alternative like fetuin or asialofetuin.

Various personal, room, and transport systems would benefit from the design which could afford effective filters with low pressure drops, Tampons Lactoferrin has been shown to be effective against various fungi, bacteria, viruses and cancers associated with the vagina. We would put lactoferrin on the tampon to directly affect these conditions.

Blood Filters

Lactoferrin membranes would enable pathogens to be cleared from the blood without a high pressure drop CWR haemofilters which require the minimum of medical training could be used.

Window, door, bed covers can be designed for hospitals and agricultural building such as stables and barns to isolate from pathogens such as flue, foot and mouth.

It is contemplated that a glycoprotein, e.g. lactoferrin (or fetuin) could be electrospun, to form a matrix, which is then attached to a carrier as discussed above, via a carbohydrate binder.

The invention claimed is:

1. An anti-pathogen device comprising:
    a carrier comprising a textile made of cotton or a cotton mix comprising polyester;
    silver particles impregnated in the carrier as an antimicrobial;
    a glycoprotein comprising sialic acid, the glycoprotein selected from a fetuin protein, an albumin protein, a lactoferrin protein, a casein protein, a lactoglobulin protein, or glycomacropeptide (GMP);
    a reactive organic-inorganic sol binder that is attached to both the glycoprotein and the carrier;
    wherein the glycoprotein is coupled to the carrier via attachment with the reactive organic-inorganic sol binder.

2. The anti-pathogen device of claim 1, wherein the glycoprotein is a fetuin protein.

3. The anti-pathogen device of claim 2, wherein the fetuin protein is fetuin or asialofetuin.

4. The anti-pathogen device of claim 1, wherein the glycoprotein is an albumin protein.

5. The anti-pathogen device of claim 4, wherein the albumin protein is albumin or α-lactalbumin.

6. The anti-pathogen device of claim 1, wherein the glycoprotein is an a lactoferrin protein.

7. The anti-pathogen device of claim 6, wherein the lactoferrin protein is lactoferrin, hololactoferrin, apolactoferrin, or asialolactoferrin.

8. The anti-pathogen device of claim 1, wherein the glycoprotein is a casein protein.

9. The anti-pathogen device of claim 8, wherein the casein protein is α-casein, β-casein, or κ-casein.

10. The anti-pathogen device of claim 1, wherein the glycoprotein is a lactoglobulin protein.

11. The anti-pathogen device of claim 10, wherein the lactoglobulin protein is β-lactoglobulin.

12. The anti-pathogen device of claim 1, wherein the reactive organic-inorganic sol binder is made using a nanotechnology sol gel process.

13. The anti-pathogen device of claim 1, wherein the device is a face mask.

14. The anti-pathogen device of claim 1, wherein the carrier is impregnated with the reactive organic-inorganic sol binder.

15. The anti-pathogen device of claim 1, wherein the device is a filter used in an air conditioning unit.

16. The anti-pathogen device of claim 1, wherein the device is a filter used in a blood filtration device.

* * * * *